(12) United States Patent
Lin et al.

(10) Patent No.: US 9,724,205 B2
(45) Date of Patent: Aug. 8, 2017

(54) BIODEGRADABLE IMPLANT FOR INTERTRANSVERSE PROCESS FUSION

(75) Inventors: Chia-Ying Lin, Ann Arbor, MI (US); Scott J. Hollister, Saline, MI (US); Frank La Marca, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 704 days.

(21) Appl. No.: 11/800,086

(22) Filed: May 3, 2007

(65) Prior Publication Data

US 2007/0270844 A1 Nov. 22, 2007

Related U.S. Application Data

(63) Continuation-in-part of application No. PCT/US2005/039938, filed on Nov. 3, 2005.

(60) Provisional application No. 60/624,658, filed on Nov. 3, 2004.

(51) Int. Cl.
*A61F 2/44* (2006.01)
*A61F 2/28* (2006.01)
*A61F 2/30* (2006.01)

(52) U.S. Cl.
CPC .............. *A61F 2/4455* (2013.01); *A61F 2/28* (2013.01); *A61F 2002/2817* (2013.01); *A61F 2002/30062* (2013.01); *A61F 2002/30599* (2013.01); *A61F 2002/30622* (2013.01); *A61F 2002/448* (2013.01); *A61F 2002/449* (2013.01); *A61F 2210/0004* (2013.01); *A61F 2250/0063* (2013.01); *A61F 2310/00365* (2013.01)

(58) Field of Classification Search
USPC ...................... 606/246–279; 623/17.11–17.16
IPC .................................. A61B 17/70; A61F 2/44
See application file for complete search history.

(56) References Cited

U.S. PATENT DOCUMENTS

| | | | | |
|---|---|---|---|---|
| 4,351,069 A | * | 9/1982 | Ballintyn et al. | 623/23.36 |
| 4,964,801 A | * | 10/1990 | Kawahara et al. | 433/173 |
| 5,015,247 A | | 5/1991 | Michelson | |
| 5,433,909 A | * | 7/1995 | Martakos | A61F 2/06 264/127 |
| 5,487,897 A | | 1/1996 | Polson et al. | |
| 5,492,697 A | | 2/1996 | Boyan et al. | |
| 5,527,864 A | | 6/1996 | Suggs et al. | |
| 5,702,446 A | * | 12/1997 | Schenck | A61F 2/30907 433/226 |
| 5,702,449 A | * | 12/1997 | McKay | A61F 2/44 623/17.16 |
| 5,876,452 A | | 3/1999 | Athanasiou et al. | |
| 5,925,074 A | * | 7/1999 | Gingras et al. | 623/1.35 |

(Continued)

OTHER PUBLICATIONS

J. Biomechanics, vol. 27, No. 4, pp. 433-444, 1994; "A Homogenization Sampling Procedure for Calculating Trabecular Bone Effective Stiffness and Tissue Level Stress," S. J. Hollister et al.

*Primary Examiner* — Jan Christopher Merene
(74) *Attorney, Agent, or Firm* — Harness, Dickey & Pierce, P.L.C.

(57) ABSTRACT

A biodegradable implant for use in intertransverse process spinal fusion having an absorbable matrix having a bone generating material disposed therein. A molded biodegradable case being made of bioabsorbable polymer can at least partially surround the absorbable matrix to carry a substantial portion of compression force relative to said absorbable matrix.

52 Claims, 8 Drawing Sheets

(56) References Cited

U.S. PATENT DOCUMENTS

| | | | |
|---|---|---|---|
| 5,976,187 A * | 11/1999 | Richelsoph | A61F 2/4455 623/17.16 |
| 5,984,967 A | 11/1999 | Zdeblick et al. | |
| 6,037,519 A * | 3/2000 | McKay | A61F 2/446 423/305 |
| 6,039,763 A * | 3/2000 | Shelokov | 623/17.16 |
| 6,139,574 A * | 10/2000 | Vacanti et al. | 623/1.44 |
| 6,149,688 A * | 11/2000 | Brosnahan et al. | 623/23.5 |
| 6,203,573 B1 | 3/2001 | Walter et al. | |
| 6,294,041 B1 * | 9/2001 | Boyce et al. | 156/275.5 |
| 6,471,724 B2 | 10/2002 | Zdeblick et al. | |
| 6,511,511 B1 | 1/2003 | Slivka et al. | |
| 6,517,477 B1 * | 2/2003 | Wendlandt | A61B 1/00156 600/114 |
| 6,600,010 B2 | 7/2003 | Mao et al. | |
| 6,613,091 B1 | 9/2003 | Zdeblick et al. | |
| 6,645,206 B1 | 11/2003 | Zdeblick et al. | |
| 6,719,795 B1 * | 4/2004 | Cornwall et al. | 623/17.11 |
| 6,726,722 B2 * | 4/2004 | Walkenhorst | A61F 2/446 606/312 |
| 6,758,849 B1 | 7/2004 | Michelson | |
| 6,758,863 B2 * | 7/2004 | Estes et al. | 623/17.16 |
| 6,783,712 B2 | 8/2004 | Slivka et al. | |
| 6,790,233 B2 * | 9/2004 | Brodke et al. | 623/17.11 |
| 6,855,169 B2 * | 2/2005 | Boyer et al. | 623/23.63 |
| 6,899,734 B2 * | 5/2005 | Castro et al. | 623/17.16 |
| 2002/0072801 A1 * | 6/2002 | Michelson | 623/17.11 |
| 2002/0128714 A1 * | 9/2002 | Manasas et al. | 623/17.15 |
| 2002/0138142 A1 * | 9/2002 | Castro et al. | 623/17.11 |
| 2002/0169507 A1 * | 11/2002 | Malone | A61B 17/7064 623/17.11 |
| 2002/0173850 A1 * | 11/2002 | Brodke et al. | 623/17.11 |
| 2002/0173851 A1 * | 11/2002 | McKay | A61F 2/4611 623/17.11 |
| 2003/0004564 A1 * | 1/2003 | Elkins et al. | 623/1.15 |
| 2003/0006534 A1 | 1/2003 | Taboas et al. | |
| 2003/0069718 A1 | 4/2003 | Hollister et al. | |
| 2003/0075822 A1 | 4/2003 | Slivka et al. | |
| 2003/0078668 A1 * | 4/2003 | Michelson | A61B 17/7059 623/17.16 |
| 2003/0093154 A1 * | 5/2003 | Estes et al. | 623/17.11 |
| 2003/0108587 A1 | 6/2003 | Orgill et al. | |
| 2003/0114854 A1 * | 6/2003 | Pavlov | A61B 17/862 606/249 |
| 2003/0120348 A1 * | 6/2003 | Brosnahan et al. | 623/23.5 |
| 2003/0149484 A1 * | 8/2003 | Michelson | A61F 2/447 623/17.16 |
| 2003/0175321 A1 | 9/2003 | Sapieszko et al. | |
| 2003/0191531 A1 * | 10/2003 | Berry | A61F 2/4455 623/17.11 |
| 2004/0049270 A1 * | 3/2004 | Gewirtz | 623/17.11 |
| 2004/0097469 A1 * | 5/2004 | Little et al. | 514/89 |
| 2004/0186569 A1 * | 9/2004 | Berry | 623/17.11 |
| 2004/0243237 A1 * | 12/2004 | Unwin et al. | 623/17.11 |
| 2004/0243241 A1 * | 12/2004 | Istephanous et al. | 623/17.14 |
| 2005/0112397 A1 * | 5/2005 | Rolfe et al. | 428/593 |
| 2005/0234550 A1 * | 10/2005 | Metz-Stavenhagen | 623/17.11 |
| 2006/0129147 A1 * | 6/2006 | Biedermann et al. | 606/61 |

* cited by examiner

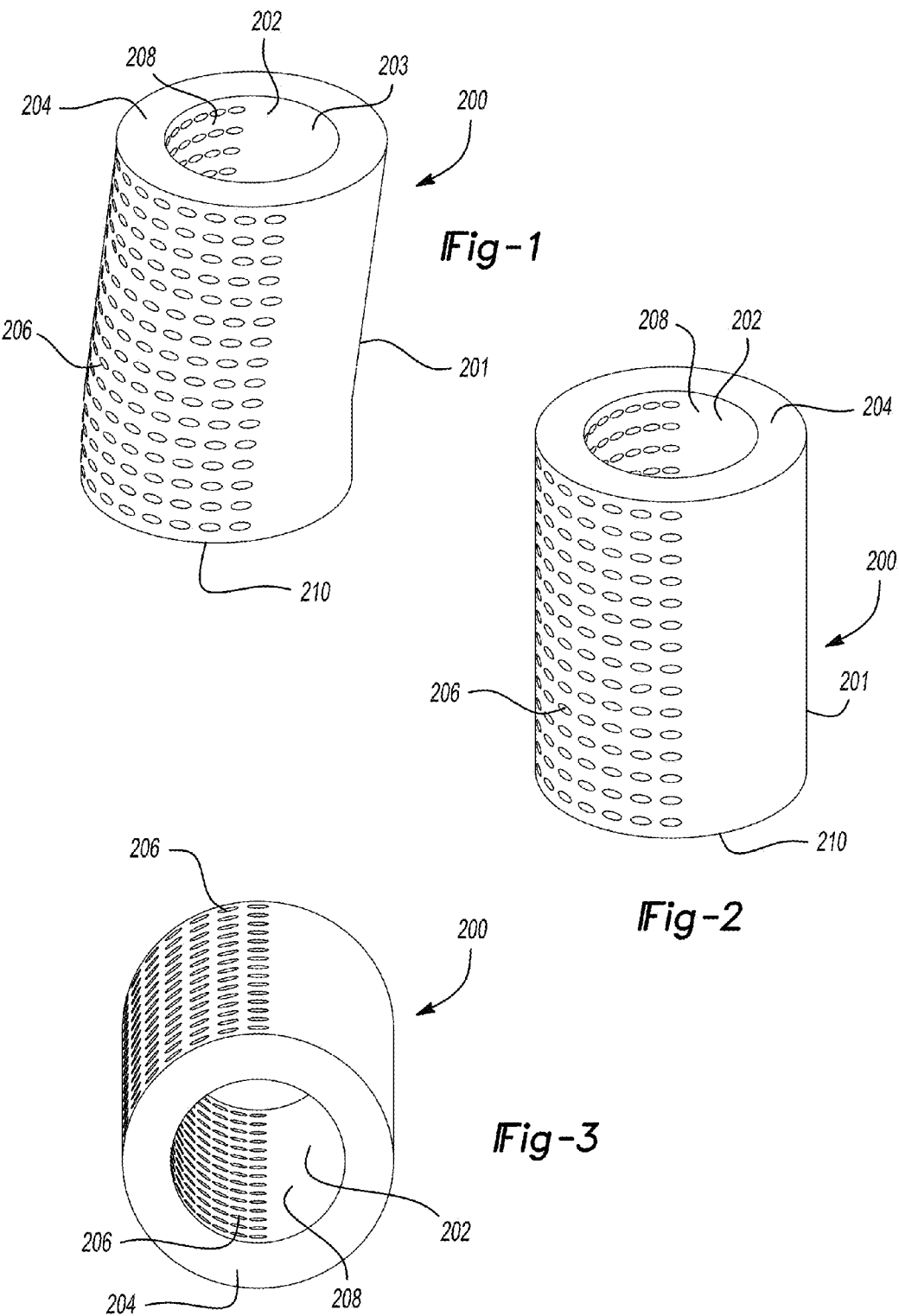

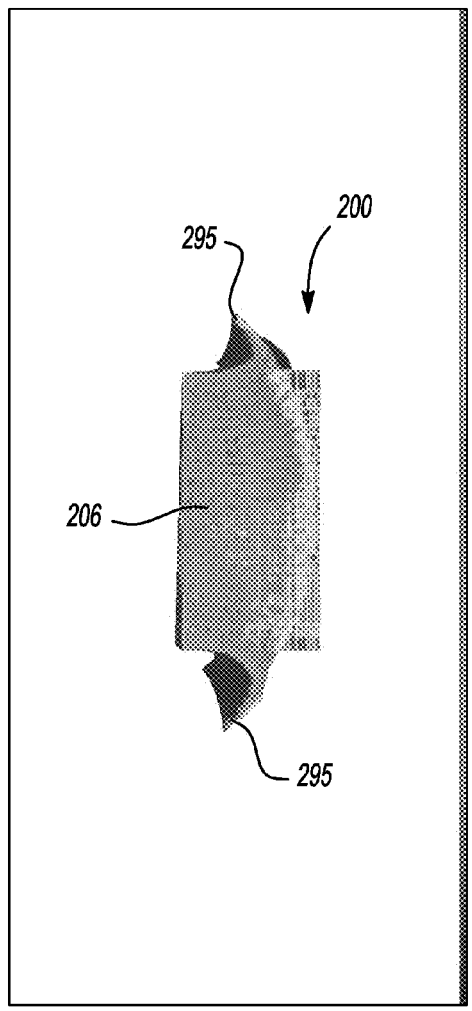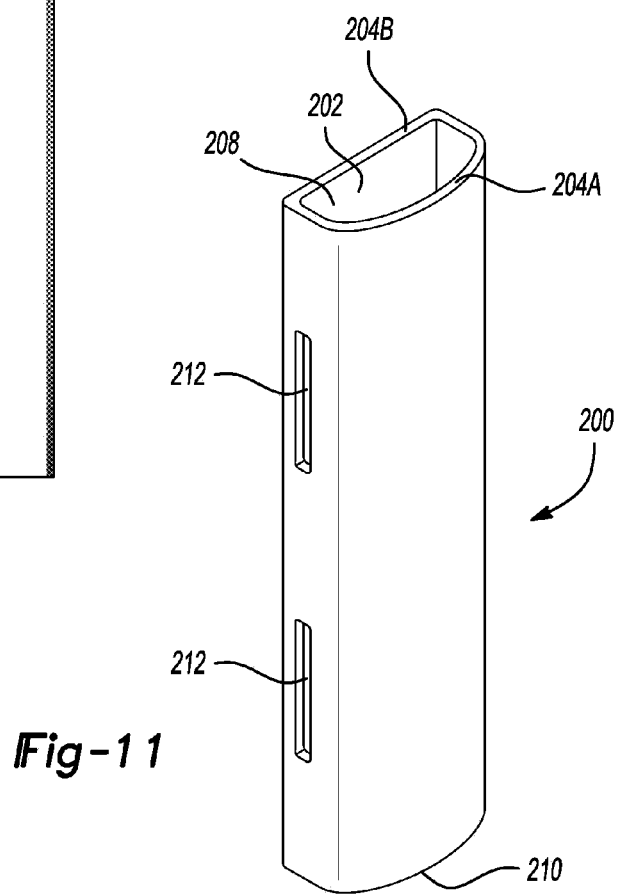
Fig-10
Fig-11

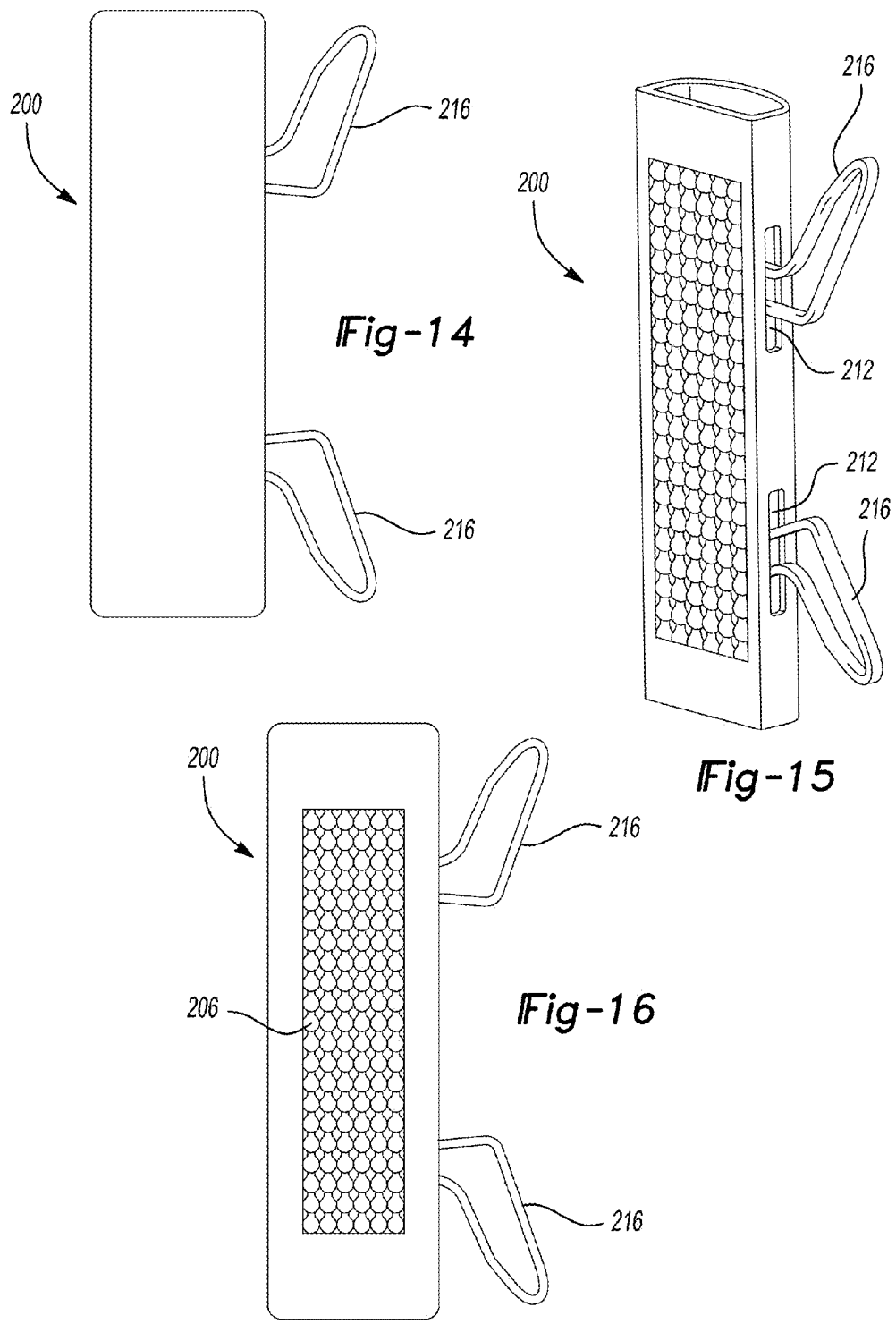

BIODEGRADABLE IMPLANT FOR INTERTRANSVERSE PROCESS FUSION

CROSS-REFERENCE TO RELATED APPLICATIONS

This application is a continuation-in-part of PCT/US2005/039938, filed on Nov. 3, 2005 and claims the benefit of U.S. Provisional Application No. 60/624,658, filed on Nov. 3, 2004. The disclosures of the above applications are incorporated herein by reference.

STATEMENT OF GOVERNMENTAL SUPPORT

This invention was made with Government support under Grant No. 5T35HL07690-24 awarded by the National Institute of Health. The Government has certain rights in this invention.

FIELD

The present invention relates to biodegradable devices and, more particularly, relates to a biodegradable fusion device for use in intertransverse process fusion to protect secondary carriers of growth factors.

BACKGROUND

Spinal fusion is a surgical procedure in which adjacent vertebrae are joined together to prevent abnormal movement. Spinal fusions are used to treat scoliosis, kyphosis, fractures and injury to the vertebrae, symptomatic degenerative disc disease, and spinal instability resulting from tumors or infection.

Currently, there are many different types of metal devices used to perform a lumbar fusion. These devices connect two or more vertebrae together, hold them in the correct position, and keep them from moving until they have a chance to grow together, or fuse. Many of the current devices that surgeons favor use metal screws that are placed through the small tube of bone, called the pedicle, and into the vertebral body. These screws are attached to metal plates or metal rods that are bolted together in the back of the spine. This combination of hardware creates a solid brace that holds the vertebrae in place. These devices are intended to inhibit or at least minimize relative movement of adjacent vertebrae that are being fused, thereby allowing a solid fusion to occur. In many cases bone grafts can be used along with a metal device to assist in the fusion process. Such a metal device provides improved stability to the fusion site and improves fusion of the bones.

Traditionally, bone grafts from the patient's iliac crest (autograft) have been used to fuse adjacent vertebrae with good results, but significant morbidity is often associated with the donor site. As healing occurs, the bone growth creates a solid fusion, which is usually complete within about three months after the procedure and continues to get stronger for one to two years. Bone morphogenetic proteins and other growth factors can be used to promote bone formation. Recently, bone morphogenetic protein (BMP-2) delivered through an absorbable collagen sponge has been found to be effective in osteoinduction and arthrodesis in anterior lumbar interbody fusion and with use of interbody fusion cages. However, the use of the collagen sponge to deliver BMP-2 in posterior intertransverse process fusion is complicated by the tendency of the paraspinal muscles to compress the sponge and allow the BMP-2 to leak away from the fusion site, requiring extremely high doses of BMP-2 to achieve fusion.

SUMMARY OF THE INVENTION

According to the present teachings, a biodegradable implant for use in intertransverse process spinal fusion is provided having an advantageous construction. The biodegradable implant comprises an absorbable matrix having a bone generating material disposed therein. A molded biodegradable case being made of bioabsorbable polymer can at least partially surround the absorbable matrix to carry a substantial portion of compression force relative to said absorbable matrix.

Further areas of applicability of the present teachings will become apparent from the description provided hereinafter. It should be understood that the detailed description and specific examples, while indicating some embodiments of the teachings, are intended for purposes of illustration only and are not intended to limit the scope of the teachings.

BRIEF DESCRIPTION OF THE DRAWINGS

The skilled artisan will understand that the drawings, described herein, are for illustration purposes only. The drawings are not intended to limit the scope of the present teachings in any way.

FIG. 1 is a perspective view of a fusion device according to the present teachings;

FIG. 2 is a side perspective view of the fusion device;

FIG. 3 is a top perspective view of the fusion device;

FIG. 10 is a lateral view of exaggerated deformation where the undistorted implant is under compression by the muscles, the implant shows some curving at the ends in this exaggerated view, however, the anterior portion remains intact and the center cavity remains open, indicating that the collagen sponge would be protected and the implant functional;

FIG. 11 is a perspective view of the back of the fusion device with slots for flange insertion;

FIG. 14 is a posterior view of the fusion device with a flange;

FIG. 15 is a side view of the fusion device with a flange;

FIG. 16 is an anterior view of the fusion device with a flange; and

DESCRIPTION OF SOME EMBODIMENTS

Figure 4:
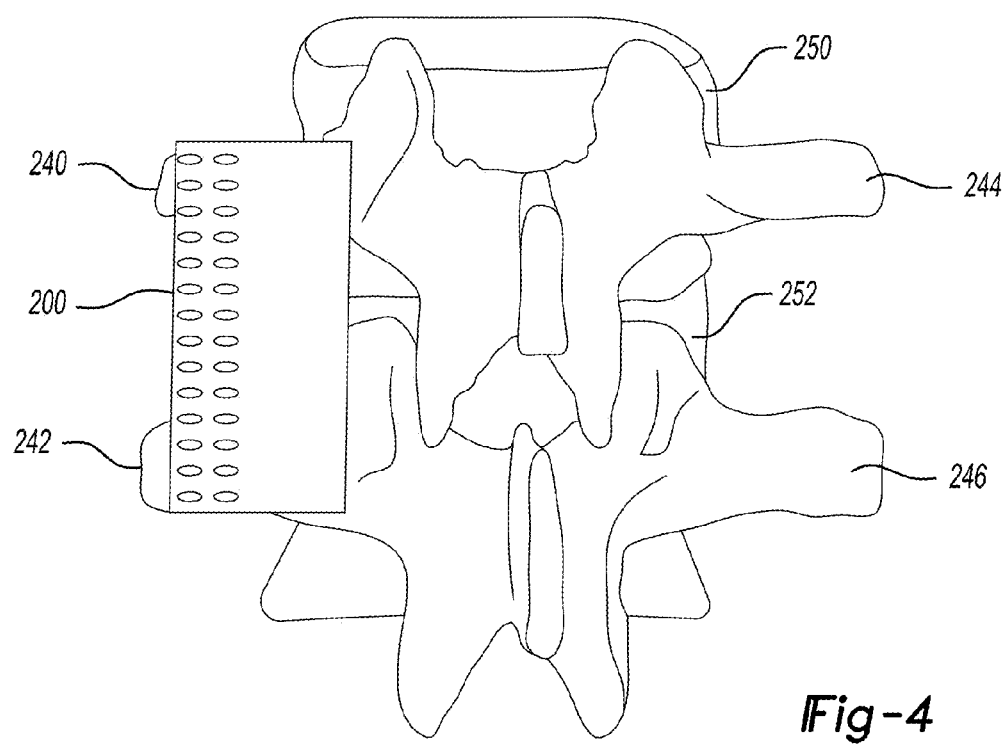
FIG. 4 is a posterior view of the fusion device in a position on the lumbar spine (L4-L5)

The following description of some embodiments is merely exemplary in nature and is in no way intended to limit the present teachings, applications, or uses. Although the present teachings will be discussed in some embodiments as relating to devices for use in spinal fusion, such discussion should not be regarded as limiting the devices to only such applications.

Spinal fusion is often used to inhibit or at least minimize motion between adjacent vertebrae. Typical surgical approaches to spinal fusion are performed from the front (anterior) or the back (posterior) of the patient. In a posterior procedure, an incision is made along the portion of the back adjacent the area of the spine to be fused. The muscles are moved or otherwise displaced to the side so as to gain access to the posterior side of the vertebrae. In some applications, a fastener, such as pedicle screws, or spinal instrumentation, such as wires, hooks, or rods, can be used to further immobilize the spine. For instance, in some cases, one or more pedicle screws may be positioned down the small bony tube created by the pedicle one arch side of the vertebra, between nerve roots. The pedicle screw extends into the bone and holds the spine rigid, thereby facilitating immobilization and thus fusion of the targeted vertebrae.

Additional surgical approaches to spinal fusion can employ interbody constructs in which the lumbar disc between adjacent vertebrae is replaced with metallic cages or bone dowels. Interbody fusion can be performed using an anterior or posterior technique and can be combined with instrumented posterolateral fusion. Traditionally, the three main posterior fusion techniques include posterolateral gutter fusion surgery, a posterior lumbar interbody fusion (PLIF) surgery, and a transforaminal lumbar interbody fusion (TLIF) surgery.

With reference to FIGS. 1-3, fusion device 200 is illustrated in accordance with some embodiments of the present teachings. Fusion device 20 is generally a biodegradable implant device useful in immobilizing adjacent vertebrae while reducing compression forces exerted upon a bone generating material disposed therein. Fusion device 200 generally comprises a biodegradable case or cage 201 having a bone generating or bioactive matrix assembly 203 disposed therein. In some embodiments, fusion device 200 can be radiolucent, transparent to x-ray, and/or transparent to CT scan analysis. In some embodiments, fusion device 200 is secured to a bone, such as a portion of a vertebra such as pedicle transverse process, spinous process, facia joint, vertebra body, and/or lamina. The implant may be designed using image-based design techniques and may be constructed using an indirect solid free-form fabrication methods, such as ink-jet thermal printing. the implant may also be fabricated using other techniques including indirect solid free-form fabrication methods such as stereo lithography (STL) and selective laser melting.

As illustrated in FIGS. 1-3, in some embodiments biodegradable case 201 can be a generally seamless member having a wall 204 defining first opened end 208, a second opened end 210, and a hollow interior volume 202. It should be appreciated that wall 204 may have various shapes, such as generally cylindrical (FIGS. 1-3), generally curved along a first portion 204A and flat along a second portion 204B (FIGS. 11-16), generally tapered, or any other seamless shape conducive to a preferred application. It should also be appreciated that multiple biodegradable cases 201 may be stacked on each other for additional vertebrae coverage. In the case of tapered wall, a first biodegradable case 201 can be inserted within a second biodegradable case 201 by virtue of the differing sizes of first opened end 208 and second opened end 210. In some embodiments, biodegradable case 201 comprises a tapered body which includes a first portion and a second portion. As shown, the second portion is not interspersed with the first portion.

In some embodiments, biodegradable case 201 comprises a plurality of pores 206 extending through wall 204 in fluid communication with hollow interior volume 202. The plurality of pores 206 can be in all or a portion of the surface area of wall 204. As will be discussed herein, hollow interior volume 202 is sized to receive bone generating or bioactive matrix assembly 203 therein. Additionally, as will be discussed herein, biodegradable case 201 is adapted to carry a substantial portion of the compression forces exerted upon fusion device 200 following implantation, such as those created during movement of the paraspinal muscle. In this regard, biodegradable case 201 protects, insulates, or otherwise minimizes compression forces exerted upon the composition of bone generating material within bone generating or bioactive matrix assembly 203 to improve the fusion rate of the targeted vertebrae. To this end, in some embodiments, biodegradable case 201 can have a wall thickness of about 0.25 mm to about 3 mm. In some embodiments, biodegradable case 201 can have a wall thickness of about 0.5 mm to about 2 mm. Additionally, in some embodiments, biodegradable case 201 can have a length from about 1 cm to about 5 cm. However, in some embodiments, biodegradable case 201 can have a length of about 3 cm for each level of spinal fusion. Likewise, in some embodiments, biodegradable case 201 can have a diameter from about 1 cm to about 2 cm. In some embodiments, biodegradable case 201 can have a diameter of about 1.5 cm.

Still referring to FIGS. 1-3, in some embodiments, the plurality of pores 206 can provide a number of advantages, such as permitting both cell and fluid permeation therethrough. In other words, the plurality of pores 206 can enable vital contributions of blood vessels from surrounding tissues, musculature, and periosteum into hollow interior volume 202 of fusion device 200 to facilitate growth of bone tissue within bone generating or bioactive matrix assembly 203. In fact, blood vessels invading hollow interior volume 202 within fusion device 200 can greatly enhance the generation of new bone. Furthermore, the proliferation of blood vessels can increase the potential of spontaneous bone regeneration within hollow interior volume 202 of fusion device 200. In some embodiments, at least some of the plurality of pores 206 may have a diameter from about 10 microns to about 3000 microns. In some embodiments, at least some of the plurality of pores 206 may have a diameter from about 20 microns to about 1000 microns.

In some embodiments, a pattern of distribution of the plurality of pores 206 may vary according to the dimensions and characteristics of the bone defect. For example, in some embodiments, a pattern of distribution of the plurality of pores 206 may cover substantially all of wall 204. In some embodiments, a pattern of distribution of the plurality of pores 206 may cover only a portion of wall 204. For example, in some embodiments, a pattern distribution of the plurality of pores 206 may cover the area of wall 204 that is in contact with a bone. With reference to FIGS. 11-16, in some embodiments the plurality of pores 206 extend along curved wall portion 204A or alternatively flat wall portion 204B. Still further, in some embodiments, fusion device 200 may have directional porosity by a design of the plurality of pores 206. It should be understood that the ranges of pore sizes, pore shapes, and pore distributions can vary depending upon the specific application and intended environment of fusion device 200. Examples of different environmental conditions encountered in spinal or other bone defects include the location of the defect, the type of defect, size of the defect, the presence or absence of periosteum, the condition of the intervertebral disc, and/or the general condition of the adjacent soft tissues covering the spinal or bone defect.

In some embodiments, the pattern of distribution of the plurality of pores only covers a portion of wall 204. For example, as shown in FIGS. 1-5, the first portion comprising a plurality of pores having a designed pattern of distribution such that the designed pattern of distribution comprises at least one third sub-portion having designed pores and at least one fourth sub-portion not having designed pores, wherein the first portion covering a contiguous section of the tubular biodegradable case and extending from the first longitudinal end to the second longitudinal end, and a second portion has a second mechanical strength and not having a designed pattern of distribution of pores wherein the second portion covering a contiguous section of the tubular biodegradable case and extending from the first longitudinal end to the second longitudinal end, wherein the second portion is wider than a widest one of the at least one fourth subportion.

Figure 5:
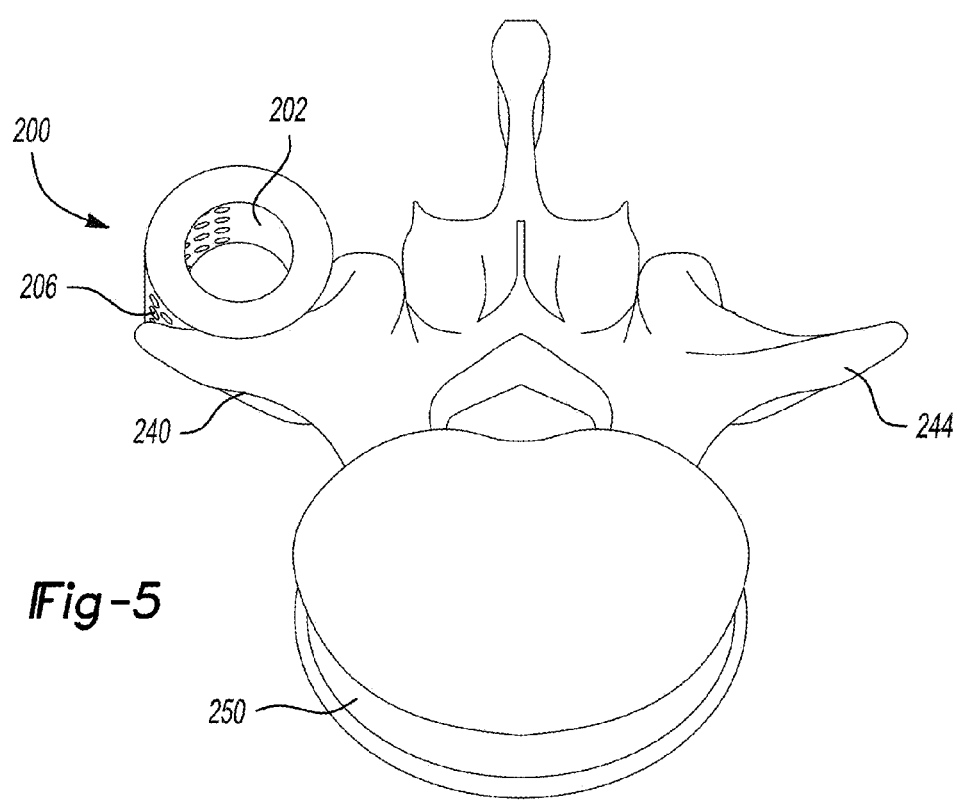
FIG. 5 is an axial view of the fusion device in a position on the lumbar spine (L4-L5)

In some embodiments, as seen in FIG. 4, the pattern of distribution of the plurality of pores may cover a part of the total surface of the wall 204. In contrast, in another embodiment, as seen in FIG. 5, where the pattern of distribution of the plurality of pores includes at least the portion of the wall 204 that is in contact with the bone, the pattern of distribution of the plurality of pores may cover a part of the wall 204.

As illustrated in FIGS. 11-16, in some embodiments, biodegradable case 201 comprises a slot or hole 212 sized to receive a protrusion, a hook (i.e. transverse process hook), a flange, a banding, or other securing device 216 to aid in securing fusion device 200 to a bone, such as via one or more pedicle screws. In some embodiments, biodegradable case 201 comprises a protrusion, flange, or hole formed directly and/or integrally with biodegradable case 201 that is operable to receive a fastener therethrough for fastening a fusion device 200 to a bone.

As described herein, biodegradable case 201 is made of a biodegradable material and, in some embodiments, can be made of a bioabsorbable and/or bioresorbable material. To this end, biodegradable case 201 can be made of a biodegradable polymer such as poly(glycolide), poly(lactide), poly($\epsilon$-caprolactone), poly(trimethylene carbonate) and poly (p-dioxanone). Additionally, biodegradable case 201 can be made of copolymers such as poly(lactide-co-glycolide), poly($\epsilon$-caprolactone-co-glycolide), and poly(glycolide-co-trimethylene carbonate). Examples of other such biodegradable polymers that can be useful with the present teachings include: lactide/tetramethylglycolide copolymers, lactide/trimethylene carbonate copolymers, lactide/$\delta$-valerolactone copolymers, lactide $\epsilon$-caprolactone copolymers, polydepsipeptides, poly(lactide)/polyethylene oxide copolymers, unsymmetrically 3,6-substituted poly(1,4-dioxane-2,5-dione), poly($\beta$-hydroxybutyrate), poly($\beta$-hydroxybutyrate)/($\beta$-hydroxyvalerate) copolymers, poly($\beta$-hydroxypropionate), poly($\delta$-valerolatone), methylmethacrylate-N-vinyl pyrrolidone copolymers, polyesteramides, polyesters of oxalic acid, polydihydropyrans, polyalkyl-2-cyanoacrylates, polyurethanes, poly(vinyl alcohol), polypeptides, poly($\beta$-maleic acid), poly($\beta$-alkanoic acid), poly(propylene fumarate) and the like. In some embodiments, a biodegradable polymer can be a statistically random copolymer, a segmented copolymer, a block copolymer, a stereocopolymer, a graft copolymer or combinations of any of the above.

In some embodiments, biodegradable case 201 can be made of a polymer composite further comprising one or more of $\beta$-tricalcium phosphate, demineralized bone, autograft bone, allograft bone, hydroxyapatite, ceramics, bone substitutes, and combinations thereof. In some embodiments, biodegradable case 201 can be made of poly(propylene fumarate)/$\beta$-tricalcium phosphate (PPF/TCP) or poly($\epsilon$-caprolactone)/$\beta$-tricalcium phosphate (PCL/TCP).

Aliphatic polyesters may be useful in the practice of the present teachings and can be typically synthesized by conventional techniques using conventional processes. For example, in a ring opening polymerization, lactone monomers can be polymerized in the presence of an organometallic catalyst and an initiator at elevated temperatures. The organometallic catalyst can be tin based, such as for example, stannous octoate, and can be present in the monomer mixture at a molar ratio of monomer to catalyst ranging from about 10,000:1 to about 100,000:1. The initiator can be typically an alkanol, a glycol, a hydroxyacid, or an amine, and can be present in the lactone monomer mixture at a molar ratio of monomer to initiator ranging from about 100:1 to about 5,000:1. The polymerization can be typically carried out at a temperature range from about 80° C. to about 220° C., or from about 160° C. to about 200° C., until the desired molecular weight and viscosity are achieved. Under these conditions, the aliphatic polyesters can typically have an average molecular weight of about 5,000 grams per mole to about 200,000 grams per mole, or about 10,000 grams per mole to about 100,000 grams per mole. Examples of suitable lactone monomers include p-dioxanone, trimethylene carbonate, $\epsilon$-caprolactone, $\delta$-valerolactone, $\beta$-butyrolactone, $\epsilon$-decalactone, 2,5-diketomorpholine, pivalolactone, $\alpha$-$\alpha$-diethylpropiolactone, ethylene carbonate, ethylene oxalate, 3-methyl-1,4-dioxane-2,5-dione, 3,3-diethyl-1,4-dioxan-2,5-dione, $\gamma$-butyrolactone, 1,4-dioxepan-2-one, 1,5-dioxepan-2-one, 1,4-dioxan-2-one, 6,8-dioxabicycloctane-7-one and combinations of two or more thereof.

In some embodiments, biodegradable case 201 can be made of a material impregnated with a variety of substances for promoting the regeneration of different tissues, such as bone and blood vessels. In some embodiments, biodegradable case 201 can be made of a material impregnated with a chemotactic substance for influencing cell-migration, an inhibitory substance for influencing cell-migration, a mitogenic growth factor for influencing cell proliferation and a growth factor for influencing cell differentiation (such as for example, insulin-like growth factor, transforming growth factor-beta, fibroblast growth factor, platelet-derived growth factor), and factors which promote neoangiogenesis (formation of new blood vessels).

As described herein, biodegradable case 201 can be filled or partially filled with bone generating or bioactive matrix assembly 203. Bone generating or bioactive matrix assembly 203 can comprise a bone generating material or bioactive material held or otherwise suspended in a matrix or suitable carrier. In some embodiments, such bone generating material or bioactive material can comprise bone grafts, bone graft substitutes, and/or fragments thereof. It should be understood, however, that bone graft fragments may naturally dispersed and be resorbed by the body unless they are rigidly held together and provided with sufficient blood supply. Such rigid hold and exposure to sufficient blood supply can be achieved using biodegradable case 201 of the present teachings. In some embodiments, a medium, such as for example, a sponge, a strip or other such suitable material for carrying a bioactive material to regulate the complex cascade of cellular events of bone repair, can be placed into the protected hollow interior volume 202 of biodegradable case 201 in addition to or as an alternative to bone grafts or other bone graft substitutes.

In some embodiments, the bioactive matrix assembly can comprise a bone generating material or bioactive material that is operatively attached to the surface of biodegradable case 201 as a coating. In some embodiments, bioactive matrix assembly 203 can comprise a mineral coating. In some embodiments, bioactive matrix assembly 203 can comprise a calcium-containing mineral. Examples of suitable calcium-containing minerals include tricalcium phosphate, hydroxyapatite, dicalcium phosphate dehydrate, calcium sulfate, calcium carbonate, carbonate-substituted hydroxyapatite. In some embodiments, bioactive matrix assembly 203 can comprise a calcium-containing mineral layer 10-1000 μm in thickness. In some embodiments, bioactive matrix assembly 203 can comprise a calcium-containing mineral layer 10-1000 μm in thickness grown via incubation in a modified simulated body fluid.

In some embodiments, the bioactive material of bone generating or bioactive matrix assembly 203 comprises a bone morphogenic protein (BMP) for use as an alternative or adjunctive bone graft material. Bone morphogenic protein (BMP) generally comprises an osteoinductive cytokine extracted from bone matrix that is capable of inducing bone formation when implanted in a fracture or surgical bone-formation site. The term BMP typically refers to a group of bone morphogenic proteins that belong to the TGF-β super family and can include the structures of eleven proteins—BMP-1 through BMP-11.

In some embodiments, recombinantly produced human bone morphogenetic protein-2 (rhBMP-2) can be used as the bioactive material of bone generating or bioactive matrix assembly 203. The purification of bovine bone-derived, bone-inductive protein has led to the cloning of recombinant human (rh) BMP-2 through rhBMP-8. BMP-2 through BMP-8 are related proteins with several common characteristics. In some embodiments, each BMP can be synthesized in a precursor form, with a hydrophobic secretory leader sequence and a substantial propeptide region. The mature protein can consists of a dimer of the carboxy-terminal portion of the propeptide molecule. All of the mature regions of these rhBMPs may contain one or more N-linked glycosylation sites and seven cysteine residues. The locations of the cysteine residues can be conserved within all members of this gene family. In some embodiments, these BMPs may prove particularly useful in spinal-fusion surgeries such as discussed herein and can be part of bone generating or bioactive matrix assembly 203 to assist in promoting osteogenic formation and healing. In some embodiments, a BMP source can include a commercial source, for example, Medtronic INFUSE® Bone Graft contains recombinant human bone morphogenetic protein (rh-BMP-2), the genetically engineered version of a naturally occurring protein that is capable of initiating bone growth in specific, targeted areas of the spine. In some embodiments, a BMP source can include a commercial source, for example, BMP-7, also known as osteogenic protein-1 (OP-1), available as Osigraft from Howmedica International S. de R. L., and available as an OP-1 implant or OP-1 Putty from Stryker Biotech. In some embodiments, a BMP source can include a commercial source, for example, rhBMP-2 available from Wyeth-Genetics Institute.

In some embodiments, among the bioactive fluids which can be added to a suitable carrier held and hollow interior volume 202 can include sterile water, saline, blood, or blood components including plasma, platelet-rich plasma, buffy coat, autologous growth factors or other concentrated blood components, red blood cells, white blood cells or platelets in any combination, as well as cryoprecipitates. In some embodiments, other bioactive fluids which can be added to a suitable carrier and held in hollow interior volume 202 can include bone marrow, as well as growth factor solutions suspensions or gels, which include any of the well known growth factors such as Platelet-Derived Growth Factor (PDGF), Transforming Growth Factor Beta (TGF-β), Insulin-Like Growth Factor (IGF), Fibroblast Growth Factor (FGF), Epidermal Growth Factor (EGF), Vascular Endothelial Growth Factor (VEGF), Bone Morphogenetic Proteins (BMPs), and vectors for gene therapy. In some embodiments, bioactives which can be added which can be added to a suitable carrier held and hollow interior volume 202 may include cellular solutions, suspensions, and materials including osteoblasts, osteoprogenitor cells, chondroblasts, stem cells, or fibroblasts as well as any solutions or suspensions containing other therapeutic agents such as antibiotics, analgesics, antithrombinolytics, or chemotherapeutic agents.

In some embodiments, the bioactive material can be a substance, or metabolic precursor thereof, which is capable of promoting growth and survival of cells and tissues, or augmenting the activity of functioning cells, as for example, blood cells, neurons, muscle, bone marrow, bone cells and tissues, and the like. In some embodiments, the bioactive material can be a nerve growth promoting substance, as for example, a ganglioside, phosphatidylserine, a nerve growth factor, brain-derived neurotrophic factor. In some embodiments, the bioactive material can be a growth factor for soft or fibrous connective tissue such as for example, a fibroblast growth factor, an epidermal growth factor, an endothelial cell growth factor, a platelet derived growth factor, an insulin-like growth factor, a periodontal ligament cell growth factor, cementum attachment extracts, and fibronectin. In some embodiments, the bioactive material can be a bone generating material, an osteogenic material, an osteoconductive material, an osteoinductive material, and/or a natural or synthetic bone morphogenic protein.

In some embodiments to promote bone growth, the bioactive material can be an osteoinductive or osteoconductive substance and/or comprise a suitable bone growth promoting agent, such as osteoinductive factor (OIF), bone morphogenetic protein (BMP) or protein derived therefrom, demineralized bone matrix, and releasing factors thereof. In some embodiments, the bioactive material that comprises bone growth promoting agents can be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. In some embodiments, the bone growth promoting substance can be in the form, such as for example, of bone chips, bone crystals or mineral fractions of bone and/or teeth, a synthetic hydroxyapatite, or other suitable form. In some embodiments, the bone growth promoting agent may further be capable of treating metabolic bone disorders such as abnormal calcium and phosphate metabolism by, for example, inhibiting bone resorption, promoting bone mineralization, or inhibiting calcification. In some embodiments, the bone growth promoting agent may also be used to promote the growth and survival of blood cells, as for example, a colony stimulating factor, and erythropoietin.

In some embodiments, the bioactive material can be mesenchymal stem cells, which can be found in surrounding mesodermal tissues and which are the precursor cells which eventually form muscle, cartilage, tendons, ligaments, connective tissues, and bone. In some embodiments, these cells can be present in these tissues and are involved in the perpetual renewal of each specific tissue, although in their earliest stage of development, these cells are not committed to becoming any given tissue. In some embodiments, an uncommitted mesenchymal stem cell found in muscle, for example, may not strictly become a muscle cell. If the mesenchymal stem cell is needed to become a bone cell, the mesenchymal stem cell may migrate to a bone defect and differentiate into a bone forming cell. In some embodiments, the mechanism for attracting these cells, and for directing them to become specific tissue cells, can be controlled by bioactive material such as for example bone morphogenic proteins and/or growth other factors. In some embodiments, the plurality of pores 206 of fusion device 200 may harness this mechanism, by allowing, for example, bone morphogenic proteins from within hollow interior volume 202 of fusion device 200 to attract mesenchymal stem cells from the surrounding connective tissues, musculature, periosteum, and/or vasculature.

In some embodiments, the choice of a suitable carrier material can be based on biocompatibility, biodegradability, mechanical properties, and interface properties. In some embodiments, the suitable carrier material can be any carrier capable of delivering BMP to an area that may facilitate spinal fusion. In some embodiments, suitable carrier has the capability of being resorbed into the body. In some embodiments, the suitable carrier material can be absorbable collagen sponge marketed by Integra LifeSciences Corporation under the trade name HELISTAT® Absorbable Collagen Hemostatic Agent. In some embodiments, the suitable carrier material can be an open cell polylactic acid polymer (OPLA). In some embodiments, the suitable carrier material comprises compositions that can be biodegradable and chemically defined such as for example, calcium sulfate, tricalcium phosphate (TCP), hydroxyapatite (HA), biphasic TCP/HA ceramic, polylactic acids and polyanhydrides.

In some embodiments, suitable carrier can be biodegradable, such as for example, bone or collagen, to permit the suitable carrier material to be broken down by the body. The suitable carrier can comprise pure proteins or extracellular matrix components and/or can comprise poly(lactic acid), poly(lacide); poly(caprolactone), poly(glycolic acid), poly (glycolide), poly(propylene fumarate), poly(dimethylglycolic) acid, poly(methylethylglycolic acid), combinations thereof, and/or copolymers thereof.

In some embodiments, the suitable carrier material can be provided in strips or sheets that can be folded to conform to hollow interior volume 202. In some embodiments, suitable carrier may extend out of openings of the devices, such as for example, the openings 208, 210 or the plurality of pores 206, to facilitate contact of the bioactive material with the highly vascularized tissue surrounding vertebrae 250, 252. In some embodiments, the bioactive material comprises a polylactic acid polymer acting as a suitable carrier for a bone morphogenic protein, for example, such as BMP-2 or rhBMP-2. Similar to the suitable carrier, the bioactive material can be a sheet that is overlapped and folds within hollow interior volume 202 of device. In some embodiments, the sheet can be long enough so that when it is folded within fusion device 200 the sheet substantially completely fills hollow interior volume 202 and can extend at least partially into at least one pore opening the plurality of pores 206. In some embodiments, bioactive material can be provided in several strips sized to fit within the hollow interior volume 202 of fusion device 200. In some embodiments, strips can be placed one against another to fill the hollow interior volume 202. In some embodiments, bioactive material can be provided in a sponge that is placed into and held within hollow interior volume 202. In some embodiments, sponge comprising bioactive material when placed within fusion device 200 substantially completely fills hollow interior volume 202 and can extend at least partially into at least one pore opening of the plurality of pores 206.

Figure 6:
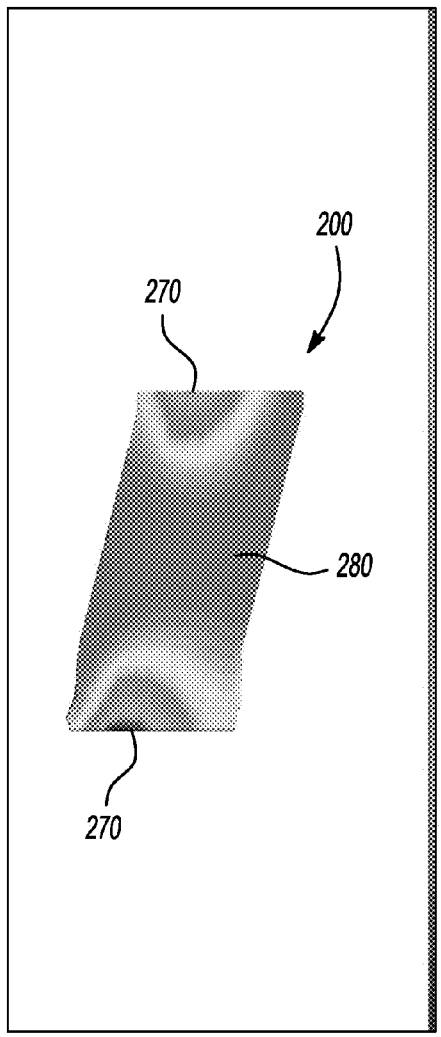
FIG. 6 is a posterior view of x-displacement where dark grey indicates zero displacement and light grey designates a displacement anteriorly towards the spine of 0.3 mm.
Figure 7:
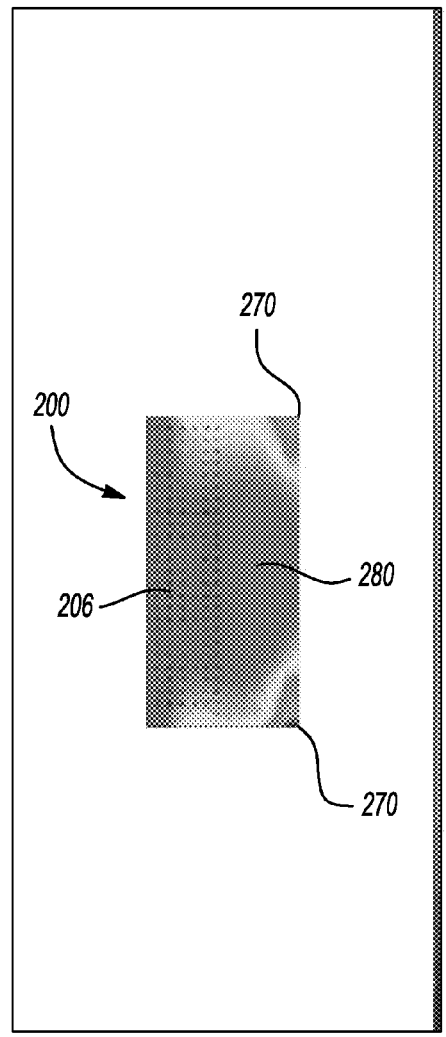
FIG. 7 is a lateral view of x-displacement where dark grey indicates zero displacement and light grey designates a displacement anteriorly (towards the spine) of 0.3 mm.
Figure 8:
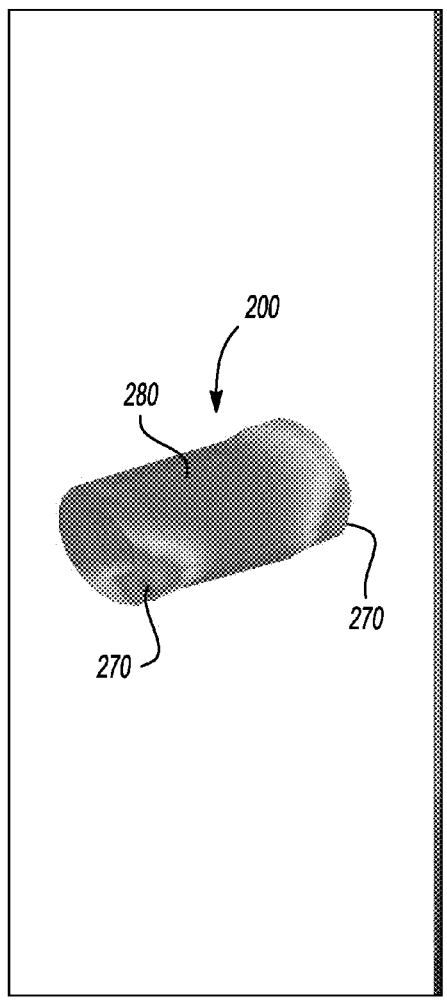
FIG. 8 is a perspective view of x-displacement where dark grey indicates zero displacement and light grey designates a displacement anteriorly towards the spine of 0.3 mm.

In some embodiments, fusion device 200 may combine two functions: the plurality of pores 206 on the anterior portion of fusion device 200 delivers growth factor toward the transverse processes to induce bone formation, and a solid wall 204 of the posterior portion of fusion device 200 prevents growth factor from diffusing into the overlying muscle to prolong growth factor delivery to the target area and control dose. In some embodiments, solid wall 204 of the posterior portion of fusion device 200 may provide the mechanical strength necessary to withstand the compressive forces exerted by the paraspinal muscles. As illustrated in FIGS. 6-10, the results of the finite-element analysis conducted modeling fusion device 200 and compressive force from the longissimus thoracis muscle (a paraspinal muscle), which lies directly posterior to the position of fusion device 200 on the vertebral transverse processes, are illustrated. FIGS. 6-8 show the calculated x-displacement of fusion device 200 under compressive force in the negative x direction (anteriorly, towards the spine). As can be seen, very little displacement occurs, with the maximum displacement of less than 0.3 mm occurring at the ends on the posterior side (shown in light grey 270 and zero is very light grey 280 in FIGS. 6-8), where the muscle is contacting fusion device 200.

During a surgical implantation procedure, a surgeon may apply bone generating or bioactive matrix assembly 203 to fusion device 200 by packing hollow interior volume 202 with bone generating or bioactive matrix assembly 203. In some embodiments, fusion device 200 can be position at or along a portion of a spine, such as for example on the lumbar spine at vertebra L4 250 and vertebra L5 252. In some embodiments, fusion device 200 can be positioned in contact with transverse process 240 of vertebra L4 250 and transverse process 242 of vertebra L5 252. In some embodiments, one fusion device 200 can be placed on transverse process 240 of vertebra L4 250 and transverse process 242 of vertebra L5 of 252 and a second fusion device 200 can be placed in contact with transverse process 244 of vertebra L4 250 and contact with transverse process 246 of vertebra L5 252. In some embodiments, fusion device can be placed in contact with adjacent transverse processes of different vertebra. In some embodiments, the plurality of pores 206 is in contact with transverse processes 240 and 242 such that bioactive material held in hollow interior volume 202 is in fluid communication with transverse processes 240 and 242.

Figure 9:
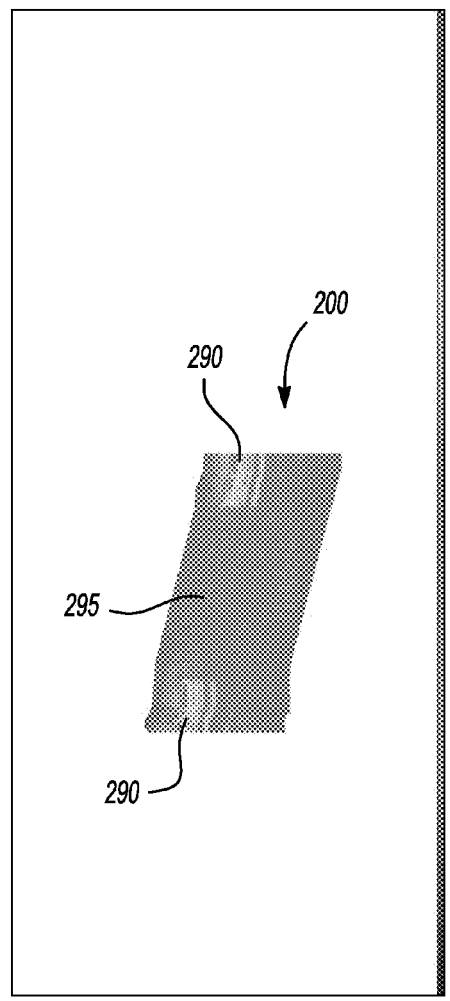
FIG. 9 is a posterior view of x-stress where dark grey indicates a stress of 0.5 MPa posteriorly and light grey designates a stress of 1.5 MPa anteriorly towards the spine and the stress is borne primarily by the posterior region of the implant where it comes in contact with the muscle.
Figure 12:
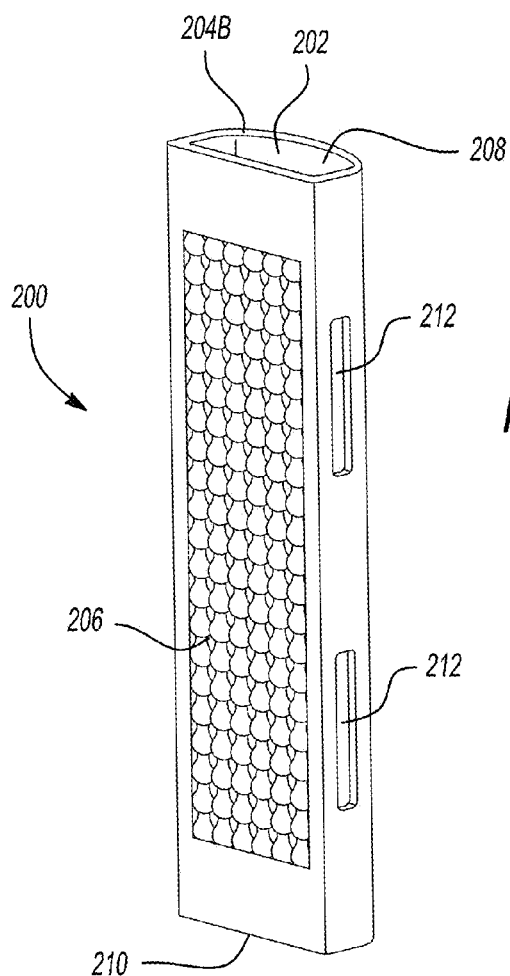
FIG. 12 is a perspective view of the back of the fusion device with slots for flange insertion.
Figure 13:
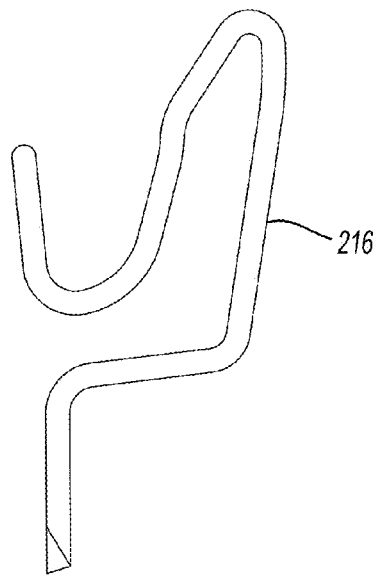
FIG. 13 is a lateral view of a flange.
Figure 17:
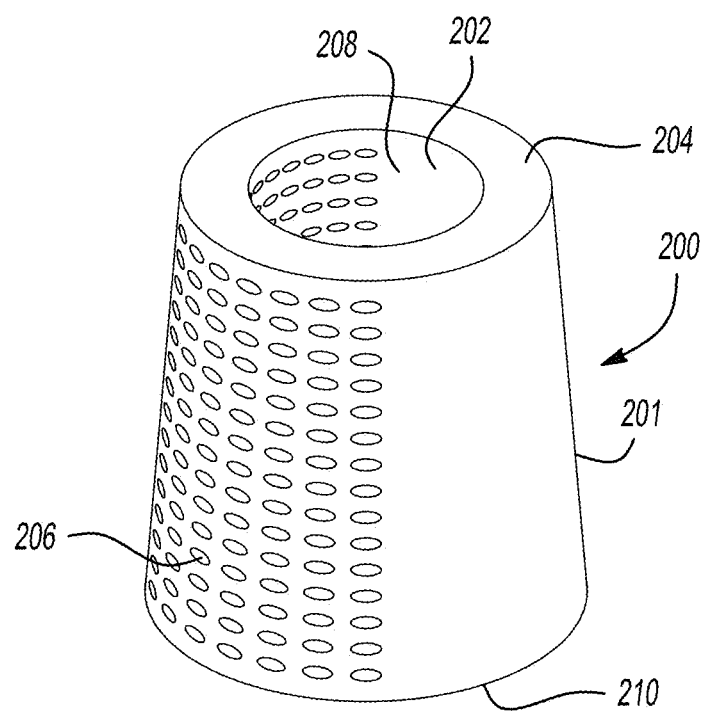
FIG. 17 is a perspective view of a tapered fusion device according to the principles of the present teachings.

Stress on the implant is shown in FIG. 9, which is a posterior view of x-stress. The highest stress is borne by the posterior side of fusion device 200 where it is contacted directly by the muscle, and is only 1.5 MPa (towards the spine and shown in black 290) as compared to 0.5 MPa posteriorly (shown in grey 295). The maximum stress of 1.5 MPa is far less than an upper limit of stress a PPF-TCP material, which has an elastic modulus of about 680 MPa. A lateral view of anteriorly exaggerated deformation fusion device 200 shown in FIG. 10 suggests that while the ends of fusion device 200 on the posterior side may curve 295, from the forces exerted by the paraspinal muscles, the plurality of pores 206 in the anterior portion and hollow interior volume 202 of fusion device 200 would remain intact. In some embodiments under extreme force from a posterior direction, bioactive material is protected by fusion device 200.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

The examples and other embodiments described herein are exemplary and not intended to be limiting in describing the full scope of compositions and methods of these teachings. Equivalent changes, modifications and variations of specific embodiments, materials, compositions and methods can be made within the scope of the present teachings, with substantially similar results.

What is claimed is:

1. A biodegradable implant, said implant comprising:
a tubular biodegradable case comprising a bioabsorbable polymer, said biodegradable case having a first longitudinal end, a second longitudinal end, and a wall, wherein the wall extends along a longitudinal axis between the first longitudinal end and the second longitudinal end, wherein the wall includes a first portion comprising a plurality of pores having a designed first pattern of distribution such that the designed first pattern of distribution comprises a first sub-portion having designed pores and a second sub-portion not having designed pores, wherein each of the first sub-portion and second sub-portion covering a contiguous section of the wall and extending substantially from the first longitudinal end to the second longitudinal end, and a second portion, wherein the second portion of the wall has no designed pattern of distribution of pores, wherein the second portion covering a contiguous section of the wall and extending from the first longitudinal end to the second longitudinal end, wherein the second portion is wider than a widest one of the second sub-portion along a width perpendicular to the longitudinal axis, and wherein the case is designed to at least partially surround an absorbable matrix and protect the absorbable matrix from a substantial portion of compression forces, wherein the first portion with the first pattern of distribution of the plurality of pores extends along about one-half of the wall.

2. The biodegradable implant according to claim 1, wherein said bioabsorbable polymer is selected from a group consisting essentially of a poly(lactic acid), a poly(lacide), a poly(caprolactone), a poly(glycolic acid), a poly(glycolide), a poly(propylene fumarate), a poly(dimethylglycolic acid), a poly(methylethylglycolic acid), one or more combinations thereof, and one or more copolymers thereof.

3. The biodegradable implant according to claim 2, wherein said bioabsorbable polymer is a composite further comprising a material selected from a group consisting essentially of β-tricalcium phosphate, demineralized bone, autograft bone, allograft bone, hydroxyapatite, one or more ceramics, one or more bone substitutes, and one or more combinations thereof.

4. The biodegradable implant according to claim 3, wherein said composite comprises a ceramic.

5. The biodegradable implant according to claim 1, further comprising the absorbable matrix which includes a bone generating material disposed therein, wherein said absorbable matrix is selected from a group consisting essentially of a collagen, a collagen sponge, a cartilage, a BMP suitable carrier, β-tricalcium phosphate, demineralized bone, autograft bone, allograft bone, hydroxyapatite, one or more ceramics, one or more bone substitutes, a hydrogel, and a synthetic sponge.

6. The biodegradable implant according to claim 5, wherein said bone generating material is selected from a group consisting essentially of BMP, recombinant BMP, OIP, OIF, one or more fragments thereof, a precursor thereof, and one or more combinations thereof.

7. The biodegradable implant according to claim 5, wherein said bone generating material is selected from a group consisting essentially of a bone marrow aspirate, a fibroblast growth factor, an epidermal growth factor, an endothelial cell growth factor, a platelet derived growth factor, an insulin-like growth factor, a periodontal ligament cell growth factor, one or more cementum attachment extracts, fibronectin, one or more stem cells, and one or more combinations thereof.

8. The biodegradable implant according to claim 1, wherein the first pattern of distribution provides a fluid communication between a bone generating material and a spinal bone.

9. The biodegradable implant according to claim 8 wherein the plurality of pores provides for directional porosity.

10. The biodegradable implant according to claim 9 wherein the directional porosity is caused by a biochemical reaction.

11. The biodegradable implant according to claim 9 wherein the directional porosity is a result of bone morphogenic proteins.

12. The biodegradable implant according to claim 1, wherein the first pattern of distribution provides a fluid communication between a bone generating material and a bodily fluid.

13. The biodegradable implant according to claim 1, further comprising:
a protrusion extending from said wall, wherein the protrusion is operable to secure said wall to a bone.

14. The biodegradable implant of claim 1 wherein the absorbable matrix further comprises a mineral coating.

15. The biodegradable implant of claim 14 wherein the mineral coating is a calcium containing mineral.

16. The biodegradable implant of claim 1, wherein the absorbable matrix is attached to a surface of the biodegradable case as a coating.

17. The biodegradable implant of claim 1, wherein the biodegradable case is manufactured using an indirect fabrication technique.

18. The biodegradable implant of claim 1, wherein the biodegradable case is manufactured using a direct fabrication technique.

19. The biodegradable implant of claim 1, wherein the first portion and the second portion are able to withstand different levels of compressive force.

20. The biodegradable implant of claim 1, wherein said wall is seamless.

21. The biodegradable implant of claim 1, wherein the second portion extends along about one-half of the wall.

22. The biodegradable implant of claim 1, wherein the first portion has a first mechanical strength and the second portion has a second mechanical strength different than the first mechanical strength.

23. The biodegradable implant of claim 22, wherein the first mechanical strength of the first portion and the second mechanical strength of the second portion are related to the first pattern of distribution of the plurality of pores and the no pattern of pore distribution and represent different mechanical strengths for withstanding compressive force.

24. The biodegradable implant of claim 1, wherein the absorbable matrix includes a bone generating material disposed therein.

25. The biodegradable implant of claim 1, wherein the tubular biodegradable case is designed for use in an intertransverse process spinal fusion.

26. The biodegradable implant of claim 1, wherein the first portion extends rectilinearly.

27. The biodegradable implant of claim 1, wherein the first portion with the first pattern of distribution of the plurality of pores extends only along a portion of the wall that is configured not to contact a bone.

28. The biodegradable implant of claim 1, wherein the first portion with the first pattern of distribution of the plurality of pores extends only along a portion of the wall that is configured to contact a bone.

29. A biodegradable implant, said biodegradable implant comprising:
a tapered body with a top, a bottom, and a wall extending along a longitudinal axis between the top and the bottom, wherein the wall including a plurality of pores distributed in a first designed pattern of distribution, wherein the plurality of pores distributed in the first designed pattern of distribution defines a first portion of the wall such that the designed pattern of distribution comprises a first sub-portion having designed pores and a second sub-portion not having designed pores, wherein each of the first sub-portion and the second sub-portion extends substantially from the top of the wall to the bottom of the wall and a second portion, wherein the second portion covering a contiguous section of the wall extending from the top of the wall to the bottom of the wall and not having a designed pattern of distribution of pores, wherein the second portion is wider than a widest one of the second sub-portion along a width perpendicular to the longitudinal axis and has a second mechanical strength, the tapered body having a hollow interior and an opening at the top of said wall, said opening being larger than an opening at the bottom of said wall, said tapered body comprising a biodegradable polymer, wherein the hollow interior is designed to hold a bone generating material disposed in a suitable carrier and protect the bone generating material from a substantial portion of compression forces by said tapered body; and said plurality of pores being in a fluid communication with said hollow interior,
wherein the longitudinal axis extends along a plane, wherein the plane segments the first portion from the second portion, and the first portion and the second portion are equivalent in area.

30. The biodegradable implant according to claim 29, wherein said biodegradable polymer is selected from a group consisting of a poly(lactic acid), a poly(lacide), a poly(caprolactone), a poly(glycolic acid), a poly(glycolide), a poly(propylene fumarate), a poly(dimethylglycolic acid), a poly(methylethylglycolic acid), one or more combinations thereof, and one or more copolymers thereof.

31. The biodegradable implant according to claim 29, wherein said biodegradable polymer is a composite further comprising a material selected from a group consisting of β-tricalcium phosphate, a demineralized bone, autograft bone, allograft bone, hydroxyapatite, one or more ceramics, one or more bone substitutes, and one or more combinations thereof.

32. The biodegradable implant according to claim 31, wherein said composite comprises a ceramic.

33. The biodegradable implant according to claim 29, wherein said suitable carrier is selected from a group consisting of collagen, a collagen sponge, a cartilage, a BMP suitable carrier, β-tricalcium phosphate, demineralized bone, autograft bone, allograft bone, hydroxyapatite, one or more ceramics, one or more bone substitutes, a hydrogel, and a synthetic sponge.

34. The biodegradable implant according to claim 29, further comprising a bone generating material disposed in a suitable carrier, wherein said bone generating material is selected from a group consisting of BMP, recombinant BMP, OIP, OIF, one or more fragments thereof, a precursor thereof, and one or more combinations thereof.

35. The biodegradable implant according to claim 34, wherein said suitable carrier comprises a biodegradable polymer selected from a group consisting of a poly(lactic acid), a poly(lacide), a poly(caprolactone), a poly(glycolic acid), a poly(glycolide), a poly(propylene fumarate), a poly(dimethylglycolic acid), a poly(methylethylglycolic acid), one or more combinations thereof, and one or more copolymers thereof.

36. The biodegradable implant according to claim 29, further comprising a bone generating material disposed in a suitable carrier, wherein said bone generating material is selected from a group consisting of a bone marrow aspirate, a fibroblast growth factor, an epidermal growth factor, an endothelial cell growth factor, a platelet derived growth factor, an insulin-like growth factor, a periodontal ligament cell growth factor, one or more cementum attachment extracts, a fibronectin, one or more stem cells, and one or more combinations thereof.

37. The biodegradable implant according to claim 29, further comprising:
a protrusion extending from said wall, wherein the protrusion is operable to secure said wall to a spine.

38. The biodegradable implant according to claim 29, wherein at least one of said plurality of pores has a pore size from about 100 microns to about 1000 microns.

39. The biodegradable implant of claim 29, wherein the first portion extends rectilinearly.

40. The biodegradable implant of claim 29, wherein the first portion has a first mechanical strength and the second portion has a second mechanical strength different than the first mechanical strength.

41. A biodegradable fusion system for use in intertransverse process spinal fusion, said biodegradable fusion system comprising:
a first biodegradable implant comprising a first tapered body having a top, a bottom, a wall, and a first hollow interior and an opening at the top of said first tapered body, said wall extends along a longitudinal axis between said top and said bottom, said opening being larger than an opening at the bottom of said first tapered body, said first tapered body comprising a biodegradable polymer, wherein the wall includes a first portion and a second portion, wherein the first hollow interior is designed to hold a first bone generating material disposed in a suitable carrier and protect the first bone generating material from a substantial portion of compression forces by said first tapered body; wherein the first portion of the first tapered body has a designed pattern of distribution of a plurality of pores covering a contiguous portion of the wall such that the designed pattern of distribution comprises a first sub-portion having designed pores and a second sub-portion not having designed pores, wherein each of the first sub-portion and the second sub-portion extends substantially from the top of the first tapered body to the bottom of the first tapered body, and wherein the second portion of the first tapered body covering a contiguous section of the wall extending from the top of the first tapered body to the bottom of the first tapered body and not having a designed pattern of distribution of pores, wherein the second portion is wider than a widest one of the second sub-portion along a width perpendicular to the longitudinal axis, and wherein the second portion is not interspersed with the first portion, said pattern of distribution of the plurality of pores being in a fluid communication with said first hollow interior;

a second biodegradable implant comprising a second tapered body having a second hollow interior and an opening at a top of said second tapered body, said opening being larger than an opening at a bottom of said second tapered body, said second tapered body comprising a biodegradable polymer;

wherein the second hollow interior is designed to hold a second bone generating material disposed in a suitable carrier and protect the second bone generating material from a substantial portion of compression forces by said second tapered body; and wherein the second tapered body has a plurality of pores in at least a portion of said second tapered body, said plurality of pores of the second tapered body being in fluid communication with said second hollow interior;

wherein said opening at said bottom of said first biodegradable implant fastens into said opening at said top of said second biodegradable implant, and wherein the first portion and second portion of the said first and second biodegradable implants each have a respective first mechanical strength and a second mechanical strength, wherein the first mechanical strength of the first portion and the second mechanical strength of the second portion represent different mechanical strengths for withstanding compressive force, the longitudinal axis extends along a plane, the plane segments the first portion from the second portion, the first portion and the second portion are equivalent in area.

42. The biodegradable fusion system according to claim 41, wherein at least one of the first tapered body or the second tapered body comprises a biodegradable polymer composite comprising one or more ceramics.

43. The biodegradable fusion system of claim 41, wherein the first portion extends rectilinearly.

44. A biodegradable implant, said implant comprising:
a tubular biodegradable case comprising a bioabsorbable polymer, said biodegradable case having a first longitudinal end, a second longitudinal end, and a wall, wherein the wall extends along a longitudinal axis between the first longitudinal end and the second longitudinal end, wherein the wall includes a first portion comprising a plurality of pores having a designed pattern of distribution such that the designed pattern of distribution comprises a first sub-portion having designed pores and a second sub-portion not having designed pores, wherein each of the first sub-portion and second sub-portion covering a contiguous section of the wall and extending substantially from the first longitudinal end to the second longitudinal end, and a second portion, wherein the second portion of the wall has no designed pattern of distribution of pores, wherein the second portion covering a contiguous section of the wall and extending from the first longitudinal end to the second longitudinal end, wherein the second portion is wider than a widest one of the second sub-portion along a width perpendicular to the longitudinal axis, and wherein the case is designed to at least partially surround an absorbable matrix and protect the absorbable matrix from a substantial portion of compression forces, wherein the longitudinal axis extends along a plane, the plane segments the first portion from the second portion and the first portion and the second portion are equivalent in area.

45. The biodegradable implant according to claim 44, wherein said bioabsorbable polymer is selected from a group consisting essentially of a poly(lactic acid), a poly(lacide), a poly(caprolactone), a poly(glycolic acid), a poly(glycolide), a poly(propylene fumarate), a poly(dimethylglycolic acid), a poly(methylethylglycolic acid), one or more combinations thereof, and one or more copolymers thereof.

46. The biodegradable implant according to claim 45, wherein said bioabsorbable polymer is a composite further comprising a material selected from a group consisting essentially of β-tricalcium phosphate, demineralized bone, autograft bone, allograft bone, hydroxyapatite, one or more ceramics, one or more bone substitutes, and one or more combinations thereof.

47. The biodegradable implant according to claim 44, further comprising the absorbable matrix which includes a bone generating material disposed therein, wherein said absorbable matrix is selected from a group consisting essentially of a collagen, a collagen sponge, a cartilage, a BMP suitable carrier, β-tricalcium phosphate, demineralized bone, autograft bone, allograft bone, hydroxyapatite, one or more ceramics, one or more bone substitutes, a hydrogel, and a synthetic sponge.

48. The biodegradable implant according to claim 47, wherein said bone generating material is selected from a group consisting essentially of BMP, recombinant BMP, OIP, OIF, one or more fragments thereof, a precursor thereof, and one or more combinations thereof.

49. The biodegradable implant according to claim 47, wherein said bone generating material is selected from a group consisting essentially of a bone marrow aspirate, a fibroblast growth factor, an epidermal growth factor, an endothelial cell growth factor, a platelet derived growth factor, an insulin-like growth factor, a periodontal ligament cell growth factor, one or more cementum attachment extracts, fibronectin, one or more stem cells, and one or more combinations thereof.

50. The biodegradable implant according to claim 44, wherein the first pattern of distribution provides a fluid communication between a bone generating material and a spinal bone.

51. The biodegradable implant according to claim 44, wherein the first pattern of distribution provides a fluid communication between a bone generating material and a bodily fluid.

52. The biodegradable implant according to claim 44, further comprising:
a protrusion extending from said wall, wherein the protrusion is operable to secure said wall to a bone.

\* \* \* \* \*